United States Patent
Darling et al.

(10) Patent No.: US 7,226,778 B2
(45) Date of Patent: *Jun. 5, 2007

(54) APPARATUS FOR NATURAL RECYCLING OF PROTEIN WASTE

(75) Inventors: Jonathan Scott Darling, Pender, NE (US); Don Scott Darling, Pender, NE (US)

(73) Assignee: Naturally Recycled Proteins, LLC, Pender, NE (US)

(*) Notice: Subject to any disclaimer, the term of this patent is extended or adjusted under 35 U.S.C. 154(b) by 618 days.

This patent is subject to a terminal disclaimer.

(21) Appl. No.: 10/607,691

(22) Filed: Jun. 30, 2003

(65) Prior Publication Data

US 2004/0265993 A1 Dec. 30, 2004

(51) Int. Cl.
*C12M 1/00* (2006.01)
*C12M 3/00* (2006.01)

(52) U.S. Cl. ............... 435/289.1; 435/290.1; 435/290.4; 71/11; 71/15; 71/18; 99/483; 99/484; 99/485; 426/53; 426/54; 426/55; 426/59; 426/443; 426/656; 426/657; 426/807; 241/38; 241/98; 452/53

(58) Field of Classification Search .............. 71/15, 71/18

See application file for complete search history.

(56) References Cited

U.S. PATENT DOCUMENTS

| | | | | |
|---|---|---|---|---|
| 3,861,293 A * | 1/1975 | Buffa et al. ............... 99/484 |
| 3,910,775 A * | 10/1975 | Jackman ............... 44/589 |
| 4,041,182 A * | 8/1977 | Erickson et al. ......... 426/59 |
| 4,099,455 A * | 7/1978 | Wenger et al. ............ 99/450.1 |
| 4,361,590 A * | 11/1982 | Wojcik ................. 426/480 |
| 4,443,540 A * | 4/1984 | Chervan et al. ......... 435/68.1 |
| 4,473,589 A * | 9/1984 | Freeman et al. ............ 426/7 |
| 4,908,220 A | 3/1990 | Shih |
| 4,959,311 A | 9/1990 | Shih |
| 5,162,129 A * | 11/1992 | Anderson et al. ......... 426/657 |
| 5,352,469 A * | 10/1994 | Peters ................ 426/478 |
| 5,713,788 A | 2/1998 | Ferket |
| 6,045,070 A * | 4/2000 | Davenport .............. 241/60 |
| 6,174,551 B1 * | 1/2001 | Griffin et al. ............ 426/53 |
| 6,299,774 B1 * | 10/2001 | Ainsworth et al. ......... 210/603 |
| 6,474,576 B1 * | 11/2002 | Oota et al. ............ 241/34 |
| 6,692,642 B2 * | 2/2004 | Josse et al. ............ 210/605 |
| 6,946,080 B2 * | 9/2005 | Perkins et al. .......... 210/754 |
| 6,958,110 B2 * | 10/2005 | Sermanni et al. ........ 162/237 |
| 2002/0197665 A1 * | 12/2002 | Dvorak ............... 435/51 |
| 2004/0112999 A1 * | 6/2004 | Byram et al. ............ 241/34 |

* cited by examiner

*Primary Examiner*—Gladys J P Corcoran
*Assistant Examiner*—Nathan A. Bowers
(74) *Attorney, Agent, or Firm*—Camille L. Urban; G. Brian Pingel

(57) ABSTRACT

An apparatus and process for naturally recycling poultry carcasses for use as a nutritional supplement, the apparatus generally consists of four modules: an enzymatic digest medium mixing assembly that self adjusts for pH; a mobile grinding assembly mounted on a truck trailer; a digesting and emulsifying assembly which includes a heated tank and separator; and a drying system. Carcasses are loaded into the grinder, and the ground carcasses are pumped into a storage tank with the enzymatic digest medium to produce a protein soluble mixture. The particle size of this mixture is then further reduced, and transported to a centralized and stationary processing plant for digesting and emulsifying. The remaining emulsified proteins are then dried. The resulting pellet-like pieces are uniformly sized for packaging.

22 Claims, 9 Drawing Sheets

APPARATUS FOR NATURAL RECYCLING OF PROTEIN WASTE

BACKGROUND OF THE INVENTION

1. Field of the Invention

The present invention relates in general to naturally recycling protein waste into feed and, more specifically, to an apparatus and process for enzymatically digesting, emulsifying and drying protein waste including feathers for use in animal feed.

2. Description of the Prior Art

A mass of waste is accumulated on a regular basis in such operations as poultry production facilities. Protein waste such as carcasses from animal production facilities pose problems for disposal. Carcasses are currently disposed of in many ways including land filling and burning. Natural gas production from waste materials is also known in the art and such processes typically also result in a byproduct which is used as animal feed or fertilizer. Some facilities process the protein waste to produce a component for animal feed but these plants often are not designed to provide a mostly closed system and, consequently, air, moisture, and other contaminants may enter creating an environment where microorganisms can multiply and destroy the quality or usefulness of the processed protein waste.

And, although there may be processing plants at which protein waste may be disposed and recycled, there is not an efficient way to remove the waste from the site to the processing plant in such time and condition as necessary for efficient processing. The timing of such disposal is essential to managing toxicity and odors yet it is not feasible for each animal production plant to also operate a processing plant for its protein waste.

Animal feed requires a protein component. In addition to the carcasses which can be processed for protein recovery, feathers are inexpensive and also high in protein, however, feathers are difficult for animals to digest And, although there are processes known for forming feather meal, often these processes require steam which, if too hot, will denature the proteins in the feathers and reduce their nutritional values. It is also known that certain bacterial strains produce keritinase which is an enzyme capable of degrading feathers and that, properly employed, such degradation can result in material that can be used in animal feeds. See U.S. Pat. Nos. 4,908,220; 4,959,311.

In addition, it is known in the art to provide a means to grind swine or poultry waste and then mix it with ingredients that will facilitate fermentation of the protein waste. See U.S. Pat. No. 5,713,788. The invention disclosed therein provides a specific grinding mechanism which includes a grinding drum with a helical groove on its outer surface in which a length of chainsaw chain, teeth side out, is positioned. This invention also does not include a way to re-circulate and thoroughly mix the ground protein and catalyst but, instead, depends on a metered application of catalyst to the ground protein waste as it moves past the grinder wherein the metering of the catalyst is triggered by the load on the grinder. This is deficient in that no additional mixing of the ground protein waste and catalyst is contemplated such that there is substantial risk that it will not be appropriately mixed and the catalytic action will be hampered.

What is needed is a way for the animal production facilities to efficiently and timely dispose of animal waste in such a way that is non-toxic and odor free. In addition, the system has to be affordable for the animal production facilities and the resultant recycled product must be usable. Preferably, a mostly closed system should be used to eliminate environmental contaminants and to provide avenues for recycling by-products. Finally, for any disposal of feathered animals, the system must provide a method of breaking down not only softer protein sources, but also feathers and in a manner that does not denature or destroy the food value of the proteins.

The first objective of the present invention is to provide a system wherein animal protein waste is processed in such a way that a portion of the system may be mobile and can be taken from one animal production facility to another or simply positioned at one facility until it reaches capacity;

The second objective of the present invention is to provide a protein processing system which is capable of degrading feathers without destroying their food value;

The third objective of the present invention is to provide a way for many different and maybe distant animal production facilities to have routine access to a processing facility;

The fourth objective of the present invention is to use natural means for recycling and breaking down the animal protein wastes and to recycle by-products of the process;

The fifth objective of the present invention is to provide an apparatus that provides mixing and grinding capabilities associated with one another in a manner that results in a mostly closed system which is an efficient process for digesting, emulsifying and drying the recycled protein waste while also providing a means for recycling other byproducts such as water and for minimizing growth of bacteria and other damaging microorganisms.

SUMMARY

The present invention provides an apparatus and process for naturally recycling poultry carcasses for use as a nutritional supplement. The apparatus generally has four modules:

1. a pH adjustable enzymatic digest medium mixing assembly, 2. a mobile grinding assembly mounted on a truck trailer, 3. a digesting and emulsifying assembly which includes a heated tank and separator, 4. and a drying system.

The enzymatic digest medium of the preferred embodiment includes protease/keritinase, inedible egg, water, and a preservative. The digest medium mixing assembly is equipped with a pH probe and monitor which triggers the addition of an acidic solution as needed to adjust the pH of the enzymatic digest.

The mobile grinding assembly can be moved from one animal production facility to another or can remain at one facility. The mobile grinding assembly of the preferred embodiment is mounted on a trailer and includes a holding tank for the enzymatic digest medium and a conveyor for loading carcasses into a grinder. The remainder of the grinding assembly is a closed system. Once through the grinder, the ground carcasses are pumped into a storage tank with the enzymatic digest medium to produce a protein solubles mixture. This mixture is then recirculated through a chopper pump for a few minutes to further reduce particle size of the ground protein waste and assure adequate mixing of the digest and the proteins and then pumped into a tanker truck for transport. Multiple batches of the protein solubles mixture can be generated so that the storage tanks are filled and emptied as many times as necessary until all the waste has been disposed. Then, the mobile grinding assembly can be moved to another location or it can simply remain until it is needed again.

The protein solubles mixture created by the mobile grinding assembly is then moved to a centralized and stationary processing plant and transferred from the tanker truck to the digesting and emulsifying assembly. The enzyme digest in the protein solubles mixture works best between about 100 and 130 degrees Fahrenheit. Therefore, the digesting and emulsifying assembly heats the mixture if needed and only periodically recirculates it until the enzymatic digest has altered the protein solubles to a mostly liquid state. The digested protein solubles are then run through an emulsifier to completely disperse the fats and proteins. The digested and emulsified proteins are then pumped into a separator tank and the bottom layer of water is drained off periodically, leaving the emulsified proteins. The water layer is then recycled back to the portion of the system where the enzymatic digest is made. The remaining emulsified proteins are then transferred to the drying system.

The dryer system uses a carrier for surface absorption of moisture, extrusion, air flow, and heat to accomplish the removal of moisture. A carrier such as cereal, soybean meal, corn or wheat mids is fed through a volumetric feeder to a mill where it is finely ground to provide ample surface area for absorption. The carrier is then conveyed to a mixer where it is mixed with the emulsified proteins until a doughlike consistency is reached. At this point, the dough is fed into an extruder to remove additional moisture and to extrude dough pellet-like pieces which are then moved by oscillating belt to the drying apparatus.

The drying apparatus includes a dryer bed which, in the preferred embodiment, is a conveyor belt enclosed in a housing. The housing alternates air flow direction and has heat zones for removing yet more moisture content and a cooling zone to return the pellet-like pieces to near room temperature. The pellet-like pieces are moved progressively through the air flow, the heat zones and the cooling zone by the conveyor. Next, the pellet-like pieces are sized and then run over a vibrating screen to separate the fines and overs. Finally, the appropriately and uniformly sized pellet-like pieces are packaged.

Other objects, features, and advantages of the present invention will be readily appreciated from the following description. The description makes reference to the accompanying drawings, which are provided for illustration of the preferred embodiment. However, such embodiment does not represent the full scope of the invention. The subject matter which the inventor does regard as his invention is particularly pointed out and distinctly claimed in the claims at the conclusion of this specification.

DESCRIPTION OF THE PREFERRED EMBODIMENT(S)

Figure 1:
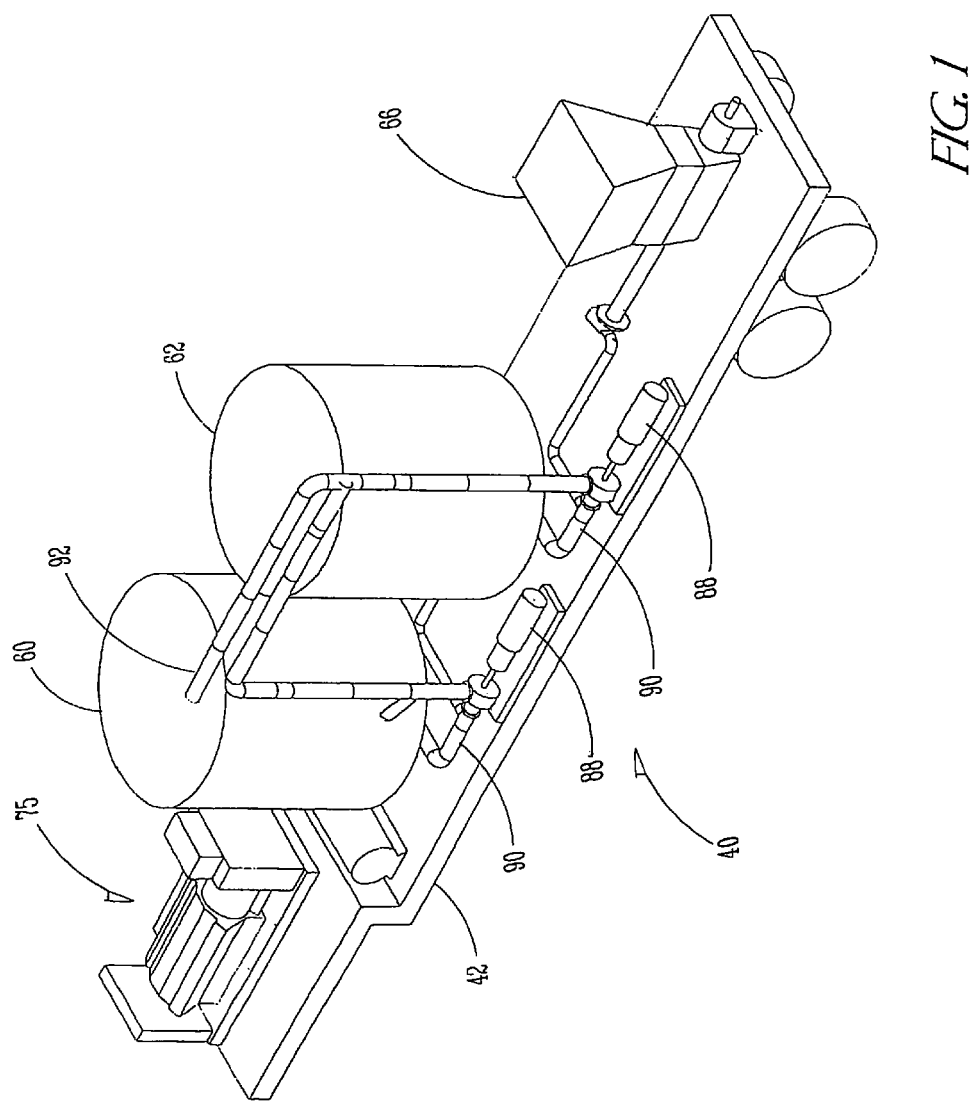
FIG. 1 is a perspective view of the mobile grinding assembly portion of the present invention.
Figure 2:
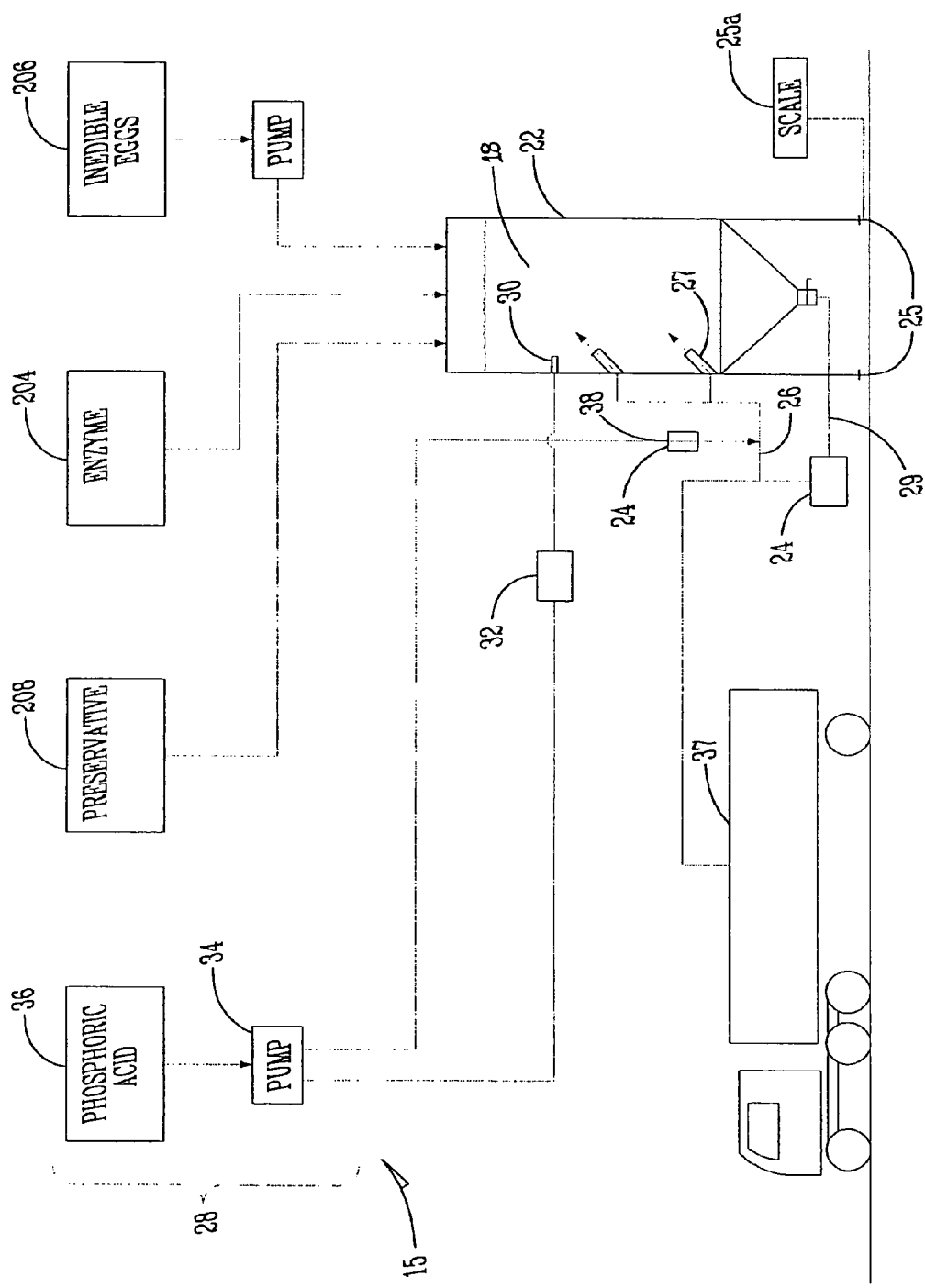
FIG. 2 is a diagram showing the enzymatic digest mixing assembly portion of the present invention.
Figure 3:
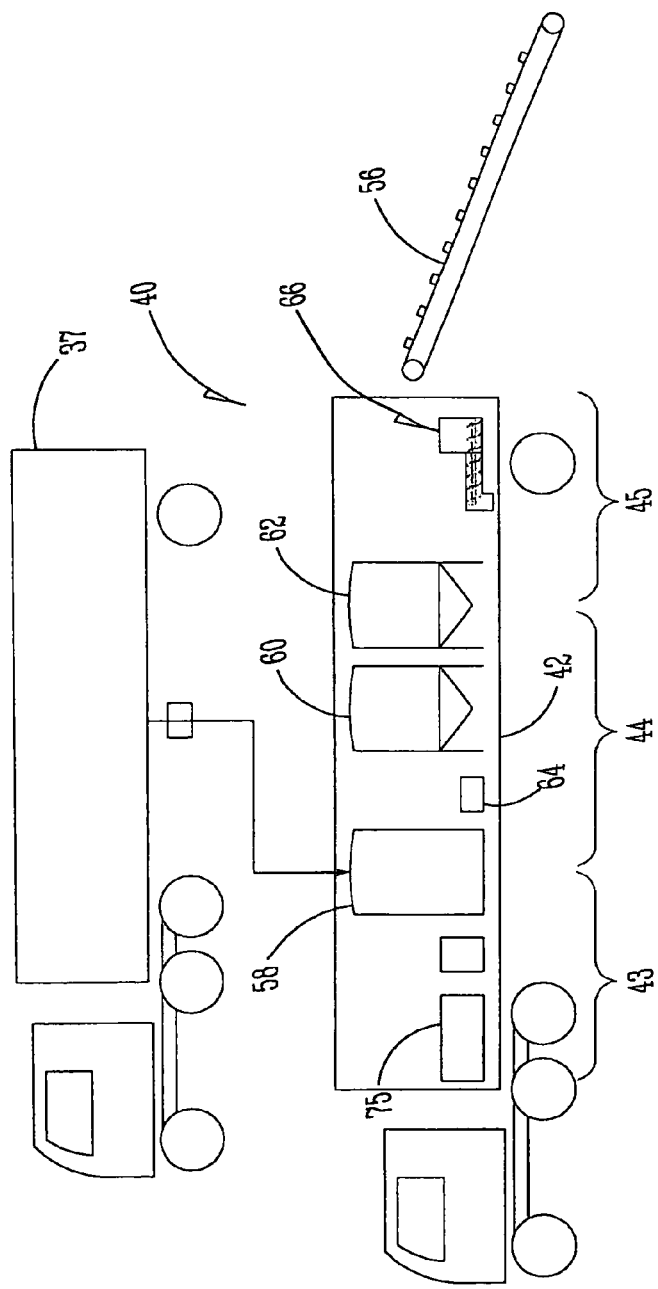
FIG. 3 is a side view of the mobile grinding assembly portion of the present invention.
Figure 4:
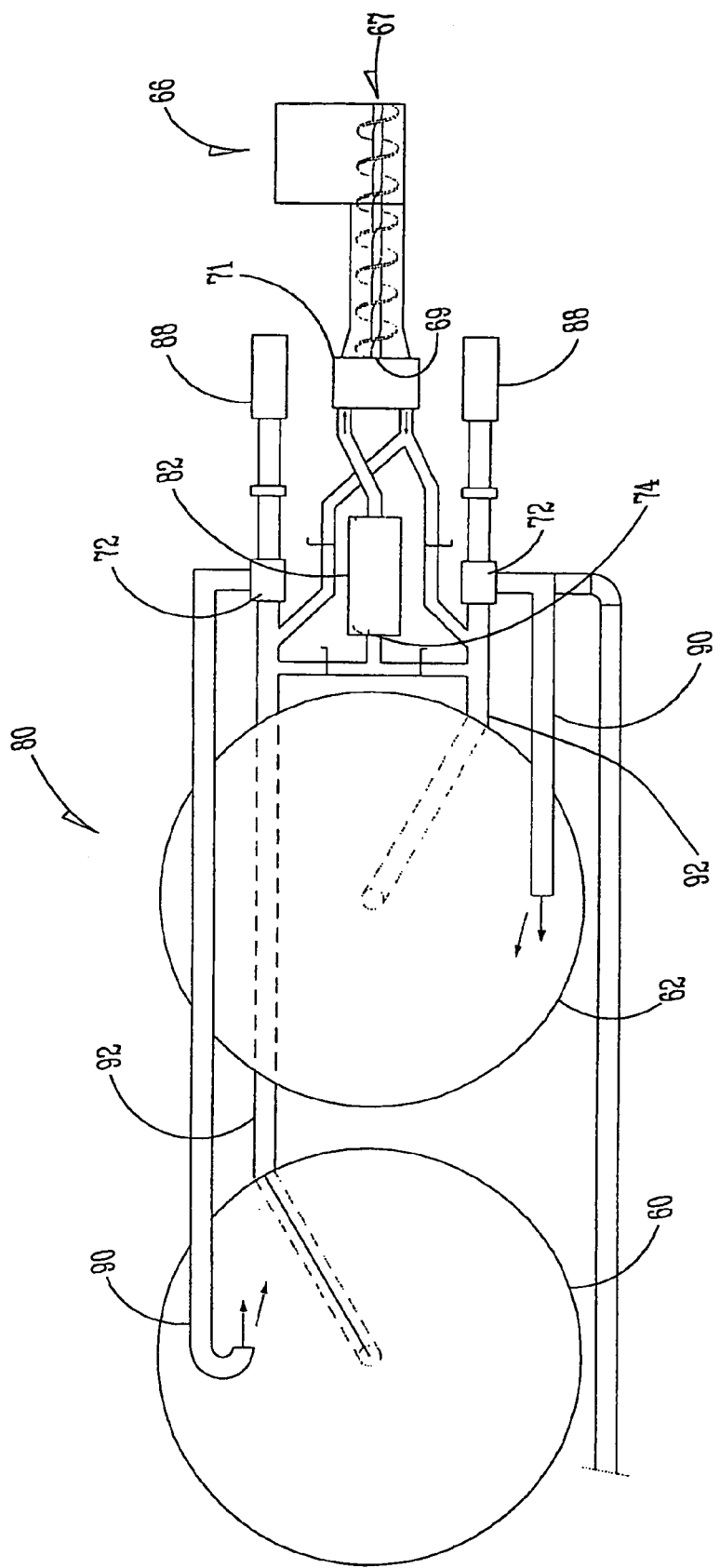
FIG. 4 is an enlarged plan view of the mobile grinding assembly of FIG. 3.
Figure 5:
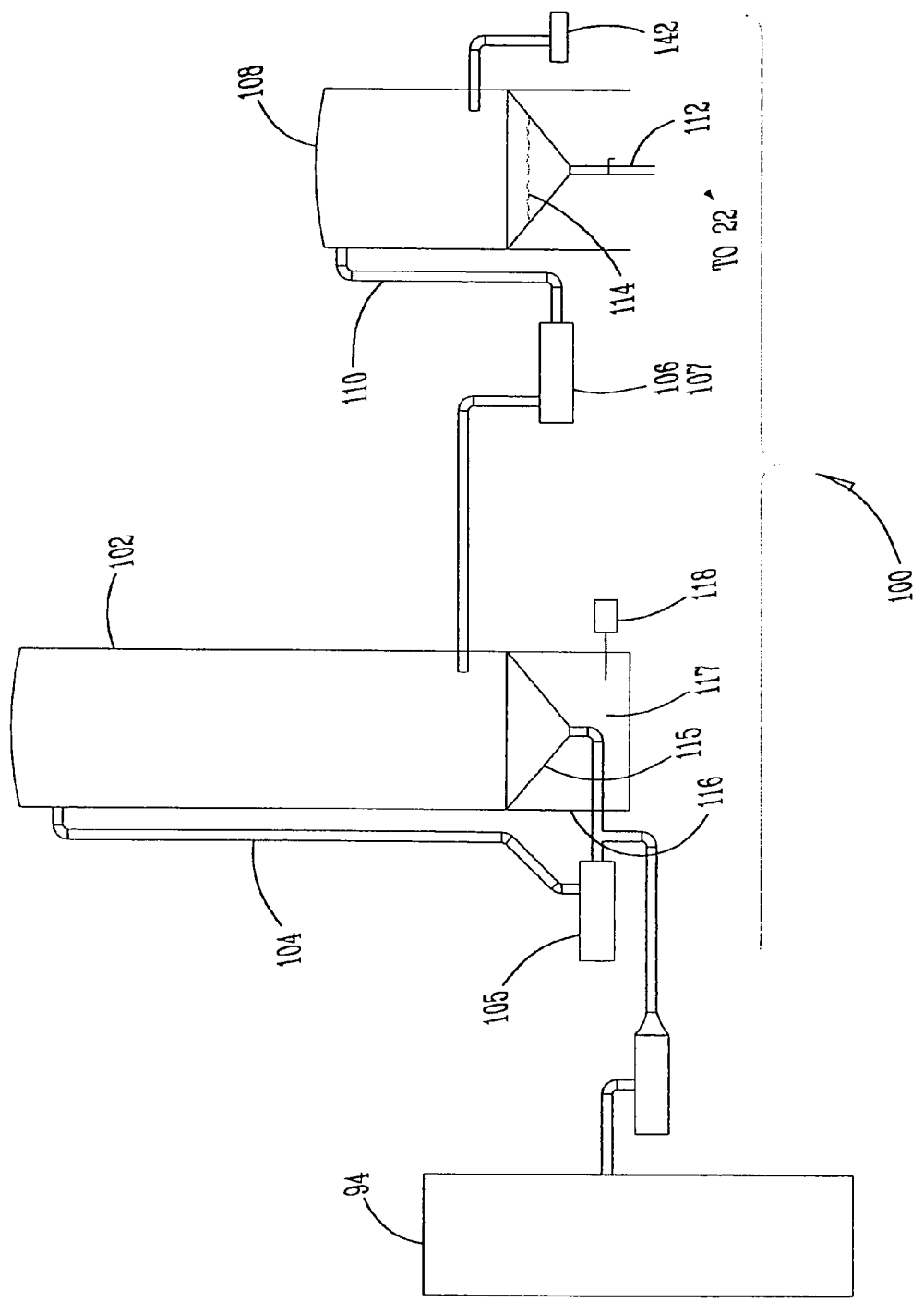
FIG. 5 is a side view of the digesting and emulsifying assembly portion of the present invention.
Figure 6:
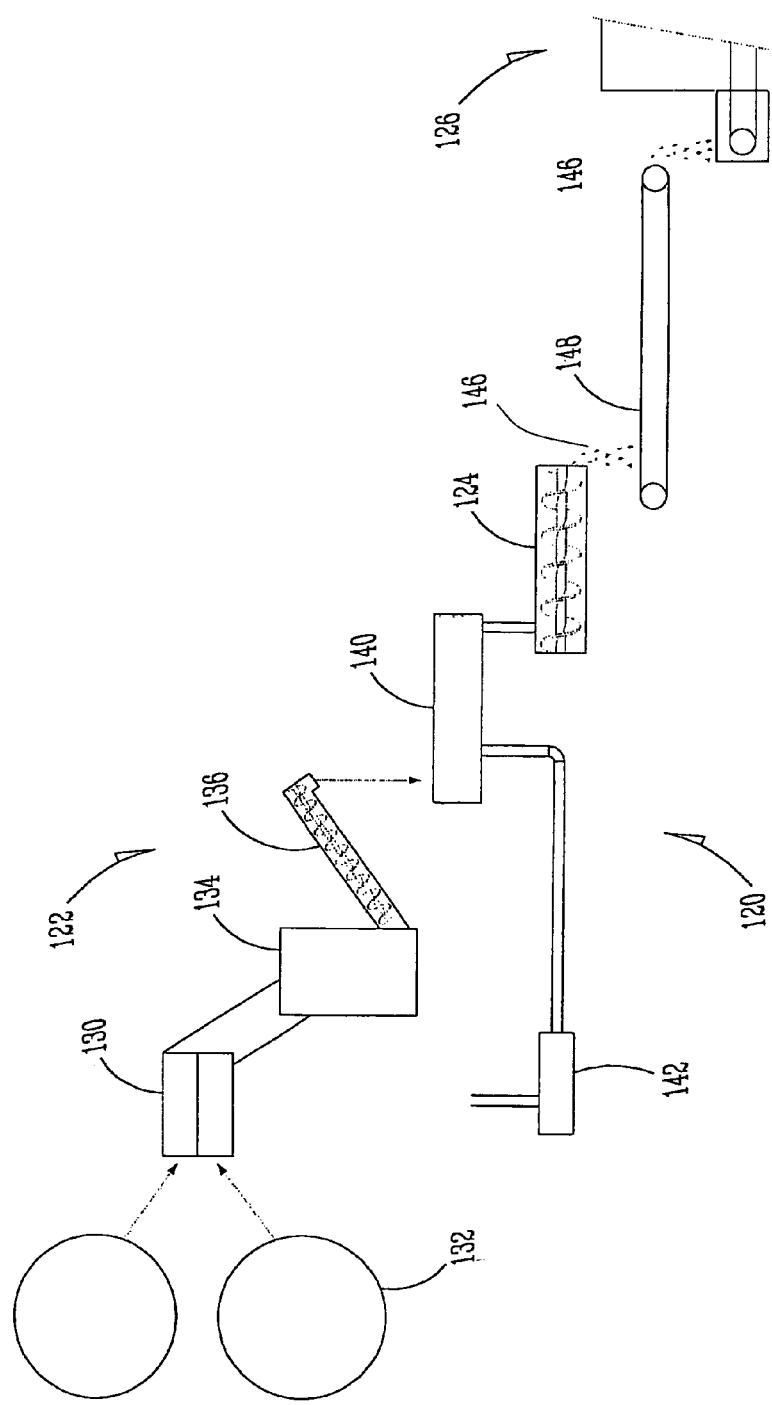
FIG. 6 is a block diagram showing the components of the dough mixing apparatus and extruder of the drying system portion of the present invention.
Figure 7:
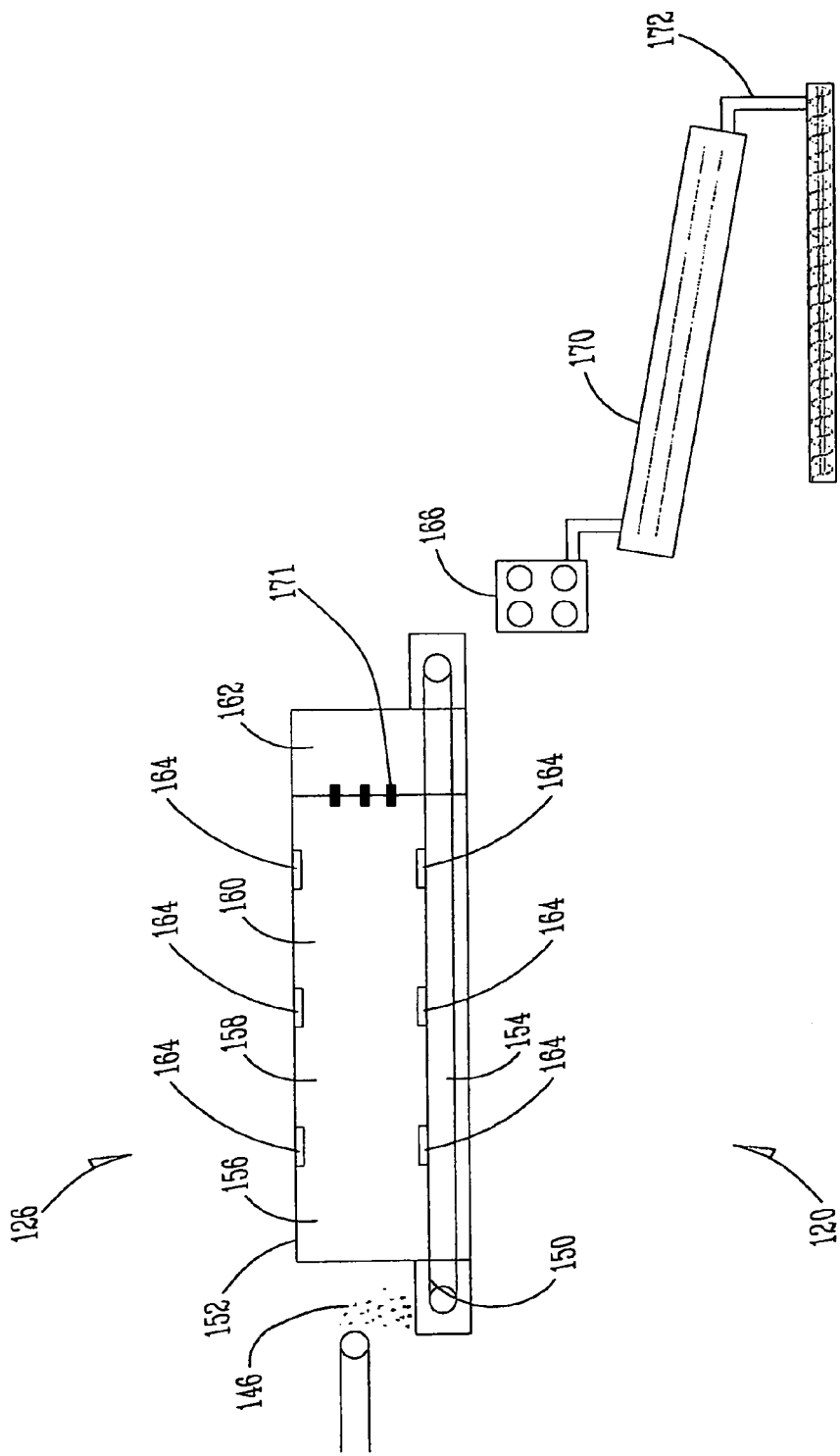
FIG. 7 is a block diagram of the drying apparatus of the drying system portion of the present invention.

The apparatus and process for naturally recycling protein waste of the present invention comprises an enzymatic digest mixing assembly shown generally as 15 in FIG. 2, a mobile grinding assembly shown generally as 40 in FIGS. 3 and 4, a digesting and emulsifying assembly shown generally as 100 in FIG. 5, and a drying system shown generally as 126 in FIGS. 6 and 7.

Figure 8:
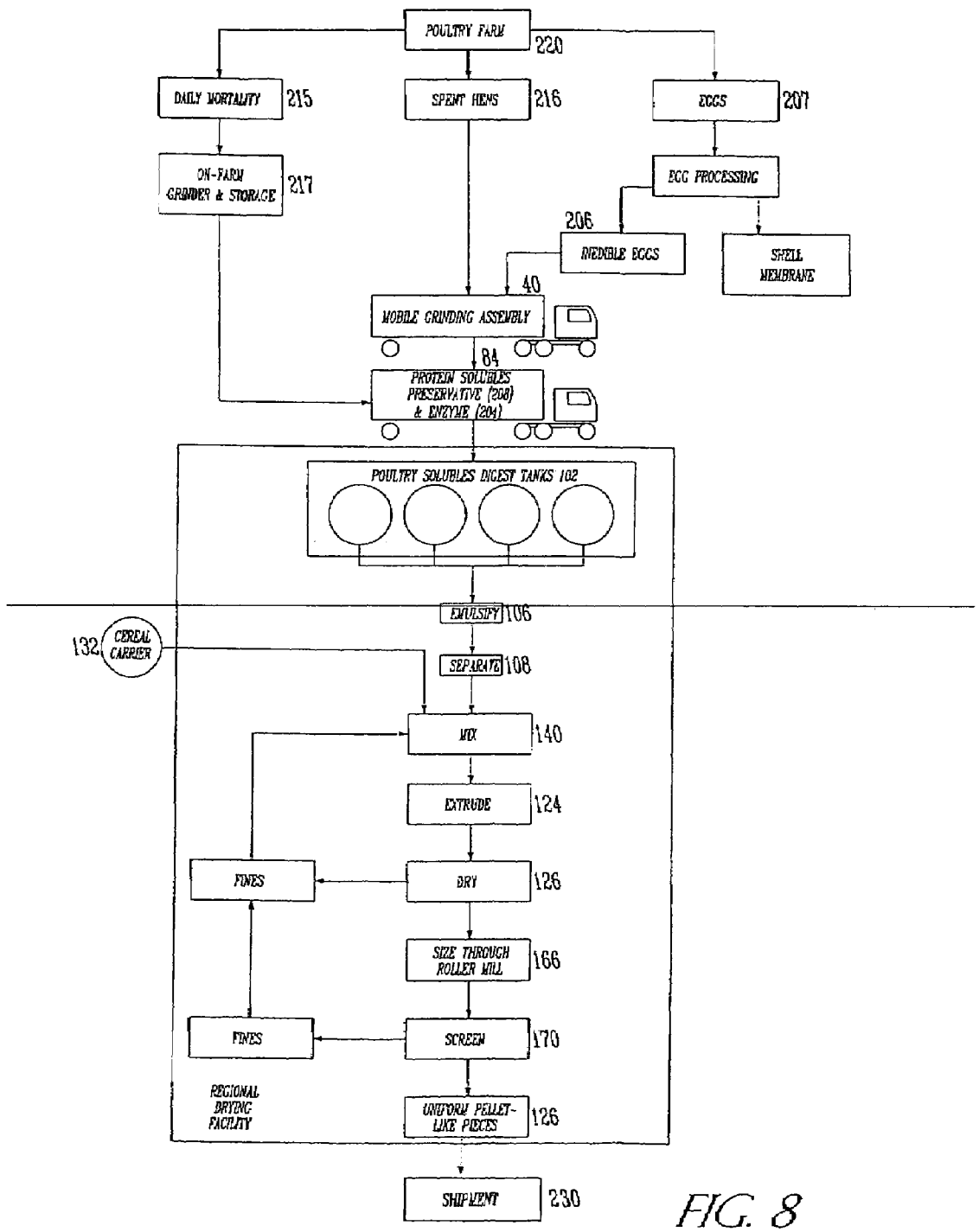
FIG. 8 is a flow diagram showing the steps for the process for natural recycling of protein waste of the present invention.

In general, the process is shown in the flow chart depicted in FIGS. 2 and 8 and requires that an enzymatic digest medium 18 of a particular pH level be prepared and stored until such time as it is needed. The medium of the preferred embodiment comprises enzymes 204, inedible egg 206, a preservative 208 and water. The enzymes 204 may include protease to break down and digest most proteins, and keritinase to aid in digestion of feathers and the preferred embodiment contemplates a mixture of preservative 2 lbs/ton, enzyme 1½ lbs/ton, and the remainder per ton of inedible egg. The preservative 208 restricts multiplication of bacteria or microorganisms which could adversely affect the end product. An example of one such preservative 208 is sodium meta-bisulfite. Although inedible egg is a logical choice when the apparatus is used in conjunction with poultry production, other fluid wastes such as outdated ice cream, molasses, milk by products, and others that include proteins, fat, and water could be appropriately substituted.

In the preferred embodiment, the pH is adjusted by measured addition of phosphoric acid to maintain an optimal level of pH 5 or within the range of about 4-6. Using phosphoric acid to effect a change in pH also adds phosphorous to the medium and, in turn, provides a high phosphorous product which may enhance the desirability of the additive for animal feed. Other acidic solutions may also be used. For example, lactic acid is one such reasonable alternative. In the case where lactic acid is used, the fermentation process which occurs as a natural consequence of the use of lactic acid, (in addition to digestion by enzymes) also acts to break down the protein waste and lowers the pH at the same time.

Protein waste which may be in the form of spent hens 216 is then ground and the enzymatic digest medium 18 and ground protein waste 216 are thoroughly mixed and recirculated through a chopper pump 88 to produce a protein solubles mixture 84. The protein solubles mixture 84 is maintained at or heated to a temperature optimal for enzyme digestive action which ranges between about 90 degrees Fahrenheit and 110 degrees Fahrenheit and recirculated periodically until the mixture is mostly liquid. The heat created by the exothermic digestive process and the friction of recirculation in certain conditions may be enough to maintain the optimal temperature and, if not, additional heat can be provided. The preferred method suggests recirculating the mixture for 1 hour every 12 hours for 3-4 days, however, the speed of the process may be increased if additional enzyme is used. When the protein solubles mixture 84 can be strained and the number of quills remaining in the strainer is acceptable, the digestion is complete. The protein solubles mixture 84 is then emulsified to disperse fats and proteins and allowed to separate. The resulting water layer 114 is drained off and recycled to be re-used for mixing enzymatic digest medium 18 and, after draining the water layer 114 several times, the emulsified proteins 110 is mixed with a carrier 132.

The carrier 132 is delivered to a high speed mixer 140 by volumetric feeder 130 and comprises a relatively high surface area to volume ratio which acts to absorb some of the moisture. Upon mixing with said emulsified proteins 110, a doughlike mixture is produced. The doughlike mixture is then extruded into a plurality of pellet-like pieces 146 and the pellet-like pieces are passed through a drying apparatus 126 which uses air flow, multiple heat zones, and at least one cooling zone for further removal of moisture. The pellet-like pieces are finally sized through a roller mill 166 to a uniform, granular size. The off-size pellet-like pieces are removed and the remaining uniform, granular pellet-like pieces can be packaged. The apparatus used to accomplish the foregoing process is described below.

The enzymatic digest mixing assembly 15 shown best in FIG. 2 is used to mix enzymes 204, inedible egg 206, and a preservative 208 with water to form an enzymatic digest medium 18 of an optimal pH level and comprises at least one enzymatic digest mixing tank 22, pumping means 24, a re-circulating assembly 26 and means for adjusting the pH level of the medium which, in the preferred embodiment, is a pH adjustment assembly 28. Said pumping means 24 of the preferred embodiment comprises a first centrifugal pump and said re-circulating assembly 26 comprises a first inductor nozzle 27 associated with said pumping means 24 and a return pipe 29 for circulating the enzymatic digest medium 18. The preferred embodiment includes load cells 25 associated with a digital scale 25a and positioned such that addition of the enzymes, preservatives, inedible egg can be measured. It is also contemplated that, in addition to external measuring of the ingredients, other internal measurement options such ultrasound and light beams may be used to monitor the amounts of each ingredient as it is added.

Said pH adjustment assembly 28 of the preferred embodiment comprises a pH probe 30, a pH monitor 32, and a first positive displacement pump 34 all electrically associated, and a supply of acidic solution 36 fluidly connected to said positive displacement pump 34 and to said mixing tank 22 through a check valve 38. Said first positive displacement pump 34 of the preferred embodiment includes a variable speed motor, preferably pumping 1-10 gallons per minute. Once said enzymatic digest medium 18 is placed in the mixing tank 22 and recirculated for at least 3-5 minute, said pH probe 30 provides pH level to the pH monitor 32. The pH monitor 32 compares the pH level 31 with an optimal level and sends a signal to the positive displacement pump 34 to move said acidic solution 36 into said mixing tank 22 where recirculation continues. The re-circulating assembly 26 continues to mix the enzymatic digest medium 18 and the pH probe 30 again measures the pH level, the monitor 32 compares the level to the optimal level, and again determines whether acidic solution 36 should be added to the mixing tank 22. When the pH level reaches the optimal level, the enzymatic digest 18 is ready to be used or stored.

The enzymatic digest medium 18 of the preferred embodiment includes, per ton, about 2½ pounds of protease and keritinase 204, about 2 pounds of preservative 208, and the remaining pounds inedible egg 206 and water. The pH is lowered to about 5 by addition of phosphoric acid 36. This pH level is optimal for this particular enzymatic digest medium, however a range from about 4-6 may be effective and the amount of enzyme may be altered according to the speed of digestion desired and the enzymes used.

Figure 4A:
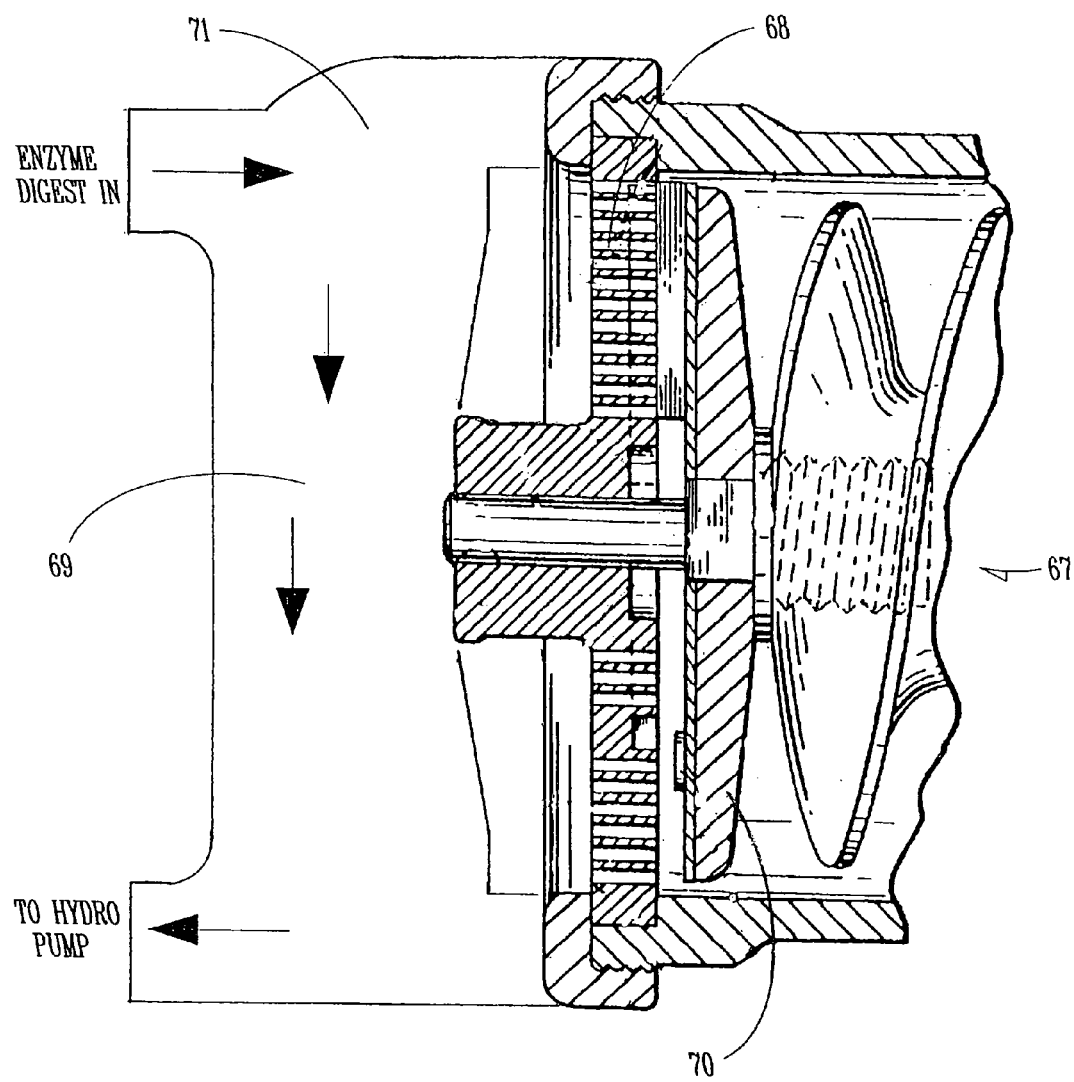
FIG. 4a is an enlarged cross-sectional view of the grinder of the grinding assembly of FIG. 4.

Once said enzymatic digest medium 18 has been prepared, it can either be stored or it can be moved via tanker truck 37 to the mobile grinding assembly 40 where it will be mixed with ground protein waste 216. Referring now to FIGS. 3 and 4, said mobile grinding assembly 40 comprises a movable platform 42 which, in the preferred embodiment, is a semi trailer, and includes a front portion 43, a mid portion 44 and a rear portion 45, a conveyor belt 56 for moving protein waste, a holding tank 58 in which said enzymatic digest 18 is stored, at least one prep tank 60, 62, and a pump 64 to move said enzymatic digest medium 18 from said holding tank 58 to said at least one prep tank 60, 62. Said mobile grinding assembly 40 further comprises grinding means 66 which, in the preferred embodiment, (shown in FIG. 4a) comprises a grinder inlet 67 positioned near said conveyor belt 56, a grinder plate 68, and a grinder outlet 69 and at least one grinder knife 70 wherein said grinder outlet 69 is positioned such that output from said grinder outlet 69 may flow by closed connection 71 into a hydro pump 82 said hydro pump 82 having a lower outlet 74. A specific example of grinding means 66 is a Weiler Meat Grinder utilizing a ⁷⁄₁₆" plate. However, different plate combinations can be used such as double-cut, double-knife combinations with a ¾" or ⅜" plate. In this situation, one knife is positioned on the inside of the grinder plate 68 and another on the outside of the grinder plate 68.

Said grinding assembly 40 further comprises mixing means 80 which, in the preferred embodiment, comprises at least one second positive displacement pump 72, which is fluidly connected to said at least one prep tank 60, 62 and to said hydro pump 82 of the grinding means 66 such that said enzymatic digest medium 18 can be moved to said hydro pump 82 where output from said grinder outlet 69 is mixed with said enzymatic digest medium 18 to form a protein solubles mixture 84. Said enzymatic digest medium 18 is pumped against said grinder outlet 69 and washes ground protein waste down into the hydro pump 82. Said lower outlet 74 of said hydro pump 82 is fluidly connected to a centrifugal chopper pump 88 which is further associated with said at least one prep tank 60 or 62 and a recirculation piping system 92 including an inductor nozzle 90. This arrangement provides a way to move said protein solubles mixture 84 through said chopper pump 88 and into said prep tank 60 via said inductor nozzle 90 which is positioned to generate a circular flow in said prep tank 60. The mixture 84 is continually recirculated through the chopper pump 88 until it is of desired consistency and thoroughly mixed. This usually requires several minutes.

The protein solubles mixture 84 is then transported to said digesting and emulsifying assembly 100 shown in FIG. 5 either via pumping it directly or by pumping it first to a tanker truck 94 and then to the assembly 100. The mobile grinding assembly 40 is a closed system wherein the grinder inlet 67 is the only input open to the environment.

Where more than one prep tank 60, 62 is present, one prep tank 60 may be recirculated or unloaded while another is being filled and recirculated. In this embodiment, a separate chopper pump is associated with each prep tank.

In one embodiment, said front portion 43 of said movable platform 42 is occupied by a power source 75 in the form of a generator, said mid portion 44 of the movable platform 42 accommodates the holding tank 58 and prep tanks 60, 62, and said rear portion 45 includes said grinding means 66 and said conveyor belt 56. Said at least one prep tank 60, 62 of the preferred embodiment is a cone-bottomed tank.

Said digesting and emulsifying assembly 100 of the preferred embodiment is stationary rather than mobile. The digesting and emulsifying assembly 100 comprises a digester tank 102 for digesting said protein solubles mixture 84, a heating means 117 and recirculation means 104 for periodic mixing including a chopper pump 105, and an emulsifier 106 fluidly connected to a pump 107, said digester tank 102, and a separator tank 108.

In the preferred embodiment, said digester tank 102 is cone-bottomed wherein the cone-bottom 115 is enclosed in a housing 116 and said heating means 117 comprises water enclosed in said housing 116 which is heated by a heating element 118 to about 120 degrees Fahrenheit. In turn, the protein solubles mixture 84 is also warmed to a temperature ranging from about 90 degrees Fahrenheit to 110 degrees Fahrenheit. The protein solubles mixture 84 is recirculated while it digests approximately 1 hour every 12 hours and for a total of 3-4 days. In certain conditions, the heat produced by the circulation friction and the exothermic digestive process may provide enough heat to maintain the digest medium at optimal temperature reducing or negating the need for adding heat.

Once digested, said protein solubles mixture 84 is pumped into said emulsifier 106 to suspend fats and proteins and produce emulsified proteins 110 which are then transferred to said separator tank 108. An example of an emulsifier suitable for this purpose in the Mincemaster Dual Plate. Said separator tank 108 comprises a closeable opening 112 fluidly associated with said enzymatic digest medium mixing tank 22 such that as a water layer 114 forms in said separator tank 108, it can be drained out and recycled for use in mixing additional digest medium 18.

Referring to FIGS. 6 and 7, the emulsified proteins 110 are moved to said drying system 120 which comprises a dough mixing apparatus 122, an extruder 124 and a drying apparatus 126. The dough mixing apparatus 122 of the preferred embodiment shown in FIG. 6 comprises a volumetric feeder 130 for measuring an absorbing carrier 132 to be mixed with said emulsified proteins 110 and which is positioned over a mill 134 for finely grinding said absorbing carrier 132. The mill 134 of the preferred embodiment is a high speed hammer mill or disc mill. A second conveyor belt 136 moves said absorbing carrier 132 from said mill 134 to a high speed continuous mixer 140. A third positive displacement pump 142 is associated with said separator tank 108 and moves said emulsified proteins 110 to said high speed mixer 140 where it is mixed with said absorbing carrier 132 to produce a doughlike mixture. In the preferred embodiment, said absorbing carrier 132 is a substance with characteristics like wheat mids, soybean meal, corn, or a previously dried material made for such purpose and the third positive displacement pump is of the variable speed variety.

The doughlike mixture is moved to said extruder 124 which pressure-forces moisture out and produces a plurality of pellet-like pieces 146. In the preferred embodiment the pellet-like pieces are 3/16" and of random length. Said pellet-like pieces 146 are extruded onto an oscillating belt 148 which distributes the pellet-like pieces 146 evenly and connects said extruder 124 to said drying apparatus 126. Additional moisture is removed by the drying apparatus 126 using heat and air movement. Said drying apparatus 126 shown best in FIG. 7 comprises a dryer bed 150 positioned to receive said pellet-like pieces 146 from said oscillating belt 148, a housing 152 through which a dryer bed conveyor belt 154 moves and conveys said pellet-like pieces 146 and which includes at least one heating zone 156, 158, 160, at least one cooling zone 162, and means to direct airflow 164. A roller mill 166 receives said pellet-like pieces 146 after they emerge from said housing 152 and sizes said plurality of pellet-like pieces 146 to a uniform size. A vibrating screen 170 is used to remove any of said plurality of said pellet-like pieces 146 which are of a non-uniform size. Means to direct airflow 164 may comprise fans positioned to alternate the flow of air to provide uniformity in drying. In the preferred embodiment, said heat zones 156, 158, 160 provide temperatures of 300, 275, and 250 Fahrenheit, in this order, such that the maximum temperature of the plurality of pellet-like pieces does not exceed 250. If the heat of the pellet-like pieces 146 exceeds this level their taste can be too bitter and the amino acids can be degraded. The cool zone 162 returns the pellet-like pieces 146 to within 10 degrees of ambient temperature. Vents 171 return the heated air from the cool zone 162 to the heat zones.

Thus, the present invention has been described in an illustrative manner. It is to be understood that the terminology that has been used is intended to be in the nature of words of description rather than of limitation.

Many modifications and variations of the present invention are possible in light of the above teachings. For example, it may be possible for all parts of the system to be made in mobile form or for none of the system to be mobile. Many different pumps are available and may be used according to need. The enzymatic digest medium can be altered to accommodate different protein/bone/feather combinations. Therefore, within the scope of the appended claims, the inventor so defines his invention:

We claim:

1. An apparatus for recycling of protein waste comprising:
   a) an enzymatic digest mixing assembly for mixing a medium and for adjusting its pH level;
   b) a mobile grinding assembly mounted on a movable platform and comprising grinding means for protein waste and mixing means for combining said ground protein waste and said enzymatic digest medium to produce a protein solubles mixture;
   c) a digesting and emulsifying assembly;
   d) a drying system comprising a dough mixing apparatus, an extruder, and a drying apparatus and
   e) said digesting and emulsifying assembly comprises:
      i. a digester tank;
      ii. heating means comprising a heating element associated with said digester tank
      iii. re-circulation means comprising a chopper pump fluidly associated with said digester tank through a re-circulation pipe and an inductor nozzle such that said protein solubles mixture in said digester tank can be heated and periodically re-circulated;
      iv. an emulsifier;
      v. a separator tank;
      vi. said emulsifier fluidly connected to said digester tank such that digested protein solubles may be emulsified and then pumped into said separator tank; and
      vii. said separator tank having a closeable opening fluidly associated with said enzymatic digest mixing tank allowing a water layer to be drained from said separator tank and recycled for use in said means for mixing an enzymatic digest medium.

2. An apparatus for recycling of protein waste as claimed in claim 1 wherein said enzymatic digest mixing assembly comprises at least one mixing tank, pumping means, a re-circulating assembly, and a pH adjustment assembly.

3. An apparatus for recycling of protein waste as claimed in claim 2 wherein said pumping means comprises a first centrifugal pump.

4. An apparatus for recycling of protein waste as claimed in claim 3 wherein said re-circulating assembly comprises a first inductor nozzle associated with said centrifugal pump and a return pipe for circulating the enzymatic digest medium.

5. An apparatus for recycling of protein waste as claimed in claim 4 wherein said pH adjustment assembly comprises:
   a) a pH probe internal to said mixing tank;
   b) a pH monitor associated with said pH probe;
   c) a first positive displacement pump; and
   d) a supply of acidic solution fluidly connected to said first positive displacement pump and to said mixing tank through a check valve wherein said pH probe provides a pH level of said enzymatic digest medium to said monitor and said monitor compares said pH level to a pH between about 4 and about 6 and signals said first positive displacement pump to pump said acidic solution to said mixing tank until said optimal pH level is reached.

6. An apparatus for recycling of protein waste as claimed in claim 5 wherein said acidic solution is phosphoric acid.

7. An apparatus for recycling of protein waste as claimed in claim 6 wherein said acidic solution is lactic acid.

8. An apparatus for recycling of protein waste as claimed in claim 1 wherein said mobile grinding assembly further comprises:
   a) said movable platform having a front portion and a mid portion and a rear portion with a conveyor belt for transporting said protein waste mounted on said rear portion;
   b) a housing mounted on said movable platform;
   c) said housing encloses a power source, a holding tank for said enzymatic digest medium, at least one cone bottomed prep tank, and a pump to move said enzymatic digest medium from said holding tank to said at least one cone bottomed prep tank;
   d) said grinding means comprises a grinder inlet positioned near said conveyor belt, a grinder plate, and a grinder outlet positioned to flow into a hydro pump with a lower outlet;
   e) said mixing means comprises a second positive displacement pump fluidly connected to said at least one cone bottomed prep tank and said hydro pump to move said enzymatic digest medium to said hydro pump wherein said lower outlet of said hydro pump is fluidly connected to a centrifugal chopper pump associated with said cone bottomed prep tank and with a re-circulation piping system and inductor nozzle such that said enzymatic digest medium and said ground protein waste can be mixed and continually re-circulated in said cone bottomed prep tank to form a protein solubles mixture.

9. An apparatus for recycling of protein waste as claimed in claim 1 wherein said digester tank comprises a cone bottom enclosed in a housing filled with fluid such that said heating element is positioned in said fluid to provide warmth to said digester tank and wherein said separator tank comprises a cone bottom in which said closeable opening is positioned.

10. An apparatus for recycling of protein waste as claimed in claim 1 wherein said dough mixing apparatus comprises:
    a) a volumetric feeder to deliver an absorbing carrier positioned over a mill for grinding said absorbing carrier;
    b) a high speed continuous mixer;
    c) a second conveyor belt to move said absorbing carrier from said feeder to said high speed continuous mixer; and
    d) a third positive displacement pump associated with said separator tank for moving emulsified protein solubles to said high speed mixer for producing a doughlike mixture.

11. An apparatus for recycling of protein waste as claimed in claim 1 wherein said extruder pressure forces moisture out and produces a plurality of pellet-like pieces and an oscillating belt connects said extruder to said drying apparatus.

12. An apparatus for recycling of protein waste as claimed in claim 11 wherein said drying apparatus comprises:
    a) a dryer bed positioned to receive said dough pellet-like pieces from said oscillating belt;
    b) a housing through which a dryer bed conveyor belt moves;
    c) said housing having at least one heating zone, at least one cooling zone, and means to direct airflow to dehydrate said pellet-like pieces;
    d) a roller mill for sizing said plurality of pellet-like pieces to uniform size; and
    e) a vibrating screen to remove any said pellet-like pieces of non-uniform size.

13. An apparatus for recycling of protein waste comprising:
    a) an enzymatic digest mixing assembly comprising pumping means, a re-circulating assembly for mixing an enzymatic digest medium, and a pH adjustment assembly;
    b) a mobile grinding assembly comprising
       i. a movable platform;
       ii. a holding tank for said enzymatic digest medium;
       iii. at least one prep tank;
       iv. a pump to move said enzymatic digest medium from said holding tank to said prep tank;
       v. grinding means for grinding protein waste; and
       vi. mixing means for combining ground protein waste and said enzymatic digest;
    c) a digesting and emulsifying assembly comprising heating means, re-circulation means, and an emulsifier; and
    d) a drying system for extruding and drying digested and emulsified protein solubles.

14. An apparatus for recycling of protein waste as claimed in claim 13 wherein said pH adjustment assembly further comprises a pH probe internal to a mixing tank, a pH monitor associated with said pH probe, and a supply of acidic solution fluidly connected to a first positive displacement pump and to said mixing tank through a check valve wherein said pH probe provides a pH level of said enzymatic digest medium to said monitor and said monitor compares said pH level to a pH between about 4 and about 6 and signals said first positive displacement pump to pump said acidic solution to said mixing tank until an optimal pH level is reached.

15. An apparatus for recycling of protein waste as claimed in claim 14 wherein said acidic solution is phosphoric acid or lactic acid.

16. An apparatus for recycling of protein waste as claimed in claim 13 wherein said grinding means comprises a grinder inlet, a grinder plate, and a grinder outlet positioned such that its output flows into a hydro pump having a lower outlet and said mixing means comprises a second positive displacement pump connected to said at least one prep tank and said hydro pump such that said enzymatic digest medium can be moved to said hydro pump to be mixed with said output from said grinder outlet to produce a protein solubles mixture, said protein solubles mixture flowing into a centrifugal chopper pump associated with said prep tank.

17. An apparatus for recycling of protein waste as claimed in claim 16 wherein said mixing means further comprises a recirculation piping system associated with a chopper pump, said prep tank, and an inductor nozzle placed within said prep tank.

18. An apparatus for recycling of protein waste as claimed in claim 13 wherein said digesting and emulsifying assembly comprises:
   a) a digester tank;
   b) heating means comprising a heating element associated with said digester tank;
   c) re-circulation means comprising a chopper pump fluidly associated with said digester tank through a re-circulation pipe and an inductor nozzle such that said protein solubles mixture in said digester tank can be heated and periodically re-circulated;
   d) an emulsifier;
   e) a separator tank;
   f) said emulsifier fluidly connected to said digester tank such that digested protein solubles may be emulsified and then pumped into said separator tank; and
   g) said separator tank having a closeable opening fluidly associated with said enzymatic digest mixing tank allowing a water layer to be drained from said separator tank and recycled for use in said means for mixing an enzymatic digest medium.

19. An apparatus for recycling of protein waste as claimed in claim 13 wherein said drying system comprises a dough mixing apparatus, an extruder, and a drying apparatus and said extruder pressure forces moisture out and produces a plurality of pellet-like pieces and an oscillating belt connects said extruder to said drying apparatus and said drying apparatus comprises:
   a) a dryer bed positioned to receive said dough pellet-like pieces from said oscillating belt;
   b) a housing through which a dryer bed conveyor belt moves;
   c) said housing having at least one heating zone, at least one cooling zone, and means to direct airflow to dehydrate said pellet-like pieces;
   d) a roller mill for sizing said plurality of pellet-like pieces to uniform size; and
   e) a vibrating screen to remove any said pellet-like pieces of non-uniform size.

20. An apparatus for recycling of protein waste comprising:
   a) an enzymatic digest mixing assembly for mixing a medium and adjusting its pH level, said enzymatic digest mixing assembly includes a mixing tank with which are associated at least a pair of load cells and a digital scale to weigh an amount of preservative, an amount of inedible egg, an amount of enzyme and an amount of water to create said enzymatic digest medium;
   b) a tanker truck for transferring said enzymatic digest medium to a mobile grinding assembly;
   c) said mobile grinding assembly mounted on a movable platform and comprising grinding means for protein waste and mixing means for combining said ground protein waste and said enzymatic digest medium to produce a protein solubles mixture;
   d) a digesting and emulsifying assembly comprising a recirculating assembly, heating means, and a return pipe fluidly associated with said enzymatic digest mixing assembly;
   e) means for transferring said protein solubles mixture from said mobile grinding assembly to said digesting and emulsifying assembly; and
   f) a drying system comprising a dough mixing apparatus, an extruder, and a drying apparatus.

21. An apparatus for recycling of protein waste as claimed in claim 20 wherein said drying apparatus comprises at least one heat zone, one cool zone, vents, and means to direct air flow such that warmth exchanged in said cool zone is returned to one of said at least one heat zones.

22. An apparatus for recycling of protein waste as claimed in claim 20 wherein said grinding means comprises a grinder inlet positioned near a conveyor belt which delivers protein waste, a grinder plate, and a grinder outlet positioned to flow into a hydro pump with a lower outlet and said mixing means comprises a second positive displacement pump fluidly connected to at least one cone bottomed prep tank and said hydro pump to move said enzymatic digest medium to said hydro pump wherein said lower outlet of said hydro pump is fluidly connected to a suction side of a centrifugal chopper pump associated with said cone bottomed prep tank and with a re-circulation piping system and inductor nozzle such that there is no opening to ambient conditions other than that of said grinder inlet.

* * * * *